United States Patent [19]
Gobron et al.

[11] 3,987,103

[45] *Oct. 19, 1976

[54] PREPARATION OF ISOPROPANOL AND ACETONE

[75] Inventors: Georges Gobron; Claude Falize; Henri Dufour, all of Melle, France

[73] Assignee: Rhone-Progil, France

[ * ] Notice: The portion of the term of this patent subsequent to Oct. 23, 1990, has been disclaimed.

[22] Filed: July 30, 1973

[21] Appl. No.: 383,617

Related U.S. Application Data

[63] Continuation-in-part of Ser. No. 878,872, Nov. 21, 1969, Pat. No. 3,767,711.

[30] Foreign Application Priority Data

Nov. 25, 1968  France .............................. 68.00500
July 7, 1969    France .............................. 69.22666

[52] U.S. Cl. ............................................. 260/593 R

[51] Int. Cl.$^2$ .................. C07C 45/00; C07C 29/14
[58] Field of Search .......................... 260/593 R, 593

[56] References Cited

UNITED STATES PATENTS

| | | | |
|---|---|---|---|
| 3,579,575 | 5/1971 | Bouniot et al. ................. | 260/593 R |
| 3,767,711 | 10/1973 | Gobron et al. .................. | 260/593 R |

OTHER PUBLICATIONS

Thüring et al., Helvetica Chimica Acta, 36 (1953) pp. 13–23.

*Primary Examiner*—James O. Thomas, Jr.
*Assistant Examiner*—James H. Reamer

[57] ABSTRACT

A process for the production of isopropanol and acetone in which isbutyraldehyde and an oxygenated salt of a metal of Groups $I_B$, $II_B$, $III_A$, $IV_A$, $V_A$, $VI_A$, $VII_A$ or VIII.

9 Claims, No Drawings

PREPARATION OF ISOPROPANOL AND ACETONE

This is a continuation-in-part of our copending application Ser. No. 878,872, filed Nov. 21, 1969, now U.S. Pat. No. 3,767,711, the disclosure of which is incorporated herein by reference.

This invention relates to a process for producing isopropanol and acetone from isobutyraldehyde by oxidizing, or oxidatively decarbonylizing, isobutyraldehyde in the liquid phase.

It has been proposed to oxidize non-aromatic compounds by means of molecular oxygen, in the liquid phase, in the presence of metal bromides, preferably manganese or cobalt bromide (British patent No. 824,116) or in the conjoint presence of a metal and bromine (U.S. Pat. No. 3,247,249). But the catalytic oxidizing action of bromine added to the action of the metal results in the production of carboxylic acids such as formic and acetic acids, and more especially isobutyric acid when the feedstock is isobutyraldehyde.

It has now been found a method of controlled oxidation which makes it possible to produce chiefly isopropanol and acetone from isobutyraldehyde.

In accordance with the practice of the present invention, isobutyraldehyde and a molecular oxygen-containing gas are contacted with a liquid reaction medium containing a liquid solvent for the isobutyraldehyde and the reaction products, and a catalyst dissolved therein and comprising one or more oxygenated salts of metals of groups $I_B$, $II_B$, $III_A$, $IV_A$, $V_A$, $VII_A$ or VIII of the Periodic Table.

Comparative tests have been carried out which show the very different results obtained with the hereinabove cited bromide catalysts and the oxygenated salt catalysts used in accordance with the present invention.

Test 1

A 1-liter balloon, equipped with a stirrer and a glass-packed distillation column, was filled with 200 g of isobutyraldehyde, 200 g of isobutyric acid as a solvent, 0.33 g of $MnBr_2.4H_2O$, 0.19 g of $CoBr_2.6H_2O$ and 5 g of NaBr. After thorough mixing, air was fed continuously at a rate of 22 liters per hour and the oxidation was carried out under refluxing of the mixture for 4 hours.

Fractional distillation of the product yielded 118 g of isobutyraldehyde, 11.2 g of an intermediate boiling distillate (chiefly esters), 236.1 g of isobutyric acid and 16.9 g of a higher boiling residue. No isopropanol nor acetone was found. The molar conversion rate of isobutyraldehyde to isobutyric acid was 14.7%.

Test 2

The same operation was carried out with the same amount of cobalt and manganese catalyst but in the form of 0.19 g of manganese acetate and 0.09 g of cobalt acetate. No NaBr was used.

Fractional distillation of the product yielded 125 g of isobutyraldehyde, 20 g of acetone, 12 g of isopropanol, 0.5 of isopropyl isobutyrate, 1.5 g of isopropyl formate, 228 g of isobutyric acid and 1.5 g of higher boiling residue. The molar conversion of isobutyraldehyde to isobutyric acid was only 11.5%, to acetone 12.5%, to isopropanol 7.2%.

It was further found that the conversion to isobutyric acid was lowered, and the conversion to acetone and isopropanol enhanced, when the oxidation was carried out continuously.

The reaction temperature, while not critical, is preferably within the range of 100° to 170° C. The pressure, likewise not critical, may be varied within a wide range, such as from atmospheric pressure, but preferably a pressure from 0.5 bar, to 5 bar, effective. The catalyst content of the bath, calculated as metal, is preferably within the range of 10 ppm to 2000 ppm by weight. Preferred metals comprising the catalyst are one or more of silver, molybdenum, vanadium, chromium, tungsten, nickel, titanium, cerium, manganese and cobalt.

A wide variety of salts may be used, including the nitrate, the sulfate, the carbonate, organic salts such as the acetate, the naphthenate and the stearate as well as a wide variety of other oxygenated salts.

As used hereinafter, the term "oxygen-containing gas" is meant to refer to and include any gas which contains molecular oxygen, or which is capable of evolving molecular oxygen under the reaction conditions prevailing in the process. For reasons of economy, air is generally the preferred molecular oxygen-containing gas.

The solvent may be preferably a chemically inert liquid which has a boiling point below 200° C. The preferred solvent which has been found to be particularly suitable for the process of the present invention is isobutyric acid. The primary advantage in using isobutyric acid is that this acid is one of the by-products of the isobutyraldehyde oxidation reaction, and hence its use as a solvent does not contaminate the reaction products with a foreign substance, and thereby facilitates separation of the desired products.

The preferred operating conditions include a temperature within the range of 110°–150° C and a pressure within the range of 1 to 4 bar, effective.

When isobutyric acid, which has a relatively low boiling point, is employed as the solvent, it is advisable either to operate under sufficient pressure to avoid entrainment of the acid in the gases leaving the reaction bath at a rate above that of its formation, or to provide a dephlegmation device to condense and reflux the vapors leaving the bath so as to maintain the bath at a constant volume. As will be appreciated by those skilled in the art, the low boiling solvent present in the starting bath is gradually replaced as the process proceeds by a high boiling bath primarily containing high boiling by-products of the oxidation reaction.

As will be demonstrated hereinafter in the examples, the use of a reactor fitted with a perforated plate for introduction of the oxygen-containing gas provides good conversion rate and high productivity.

The isobutyraldehyde conversion rate, per passage, can be as high as 85%, and the practical molar yields for the primary three products of the reaction are as follows:

| | |
|---|---|
| Isopropanol | 20–40 % |
| Acetone | 35–45 % |
| Isobutyric acid | 0–15 % |

As will be understood, the impurities frequently found in the final reaction mixture include isopropyl formate, isopropyl isobutyrate, acetic acid, propionic acid, methyl ethyl ketone, diacetyl, di-isopropyl ether and di-isopropyl ketone. The gaseous by-products are generally:

| | |
|---|---|
| Carbon monoxide | 70–80 % by volume |
| Carbon dioxide | 10–20 % by volume |
| Propane | 10–15 % by volume |

Water is also produced in the reaction of the present invention. The water content depends upon the conversion rate.

It has been found that the catalyst in the reaction bath serves as a partial destroyer of peroxides which are formed as by-products of the reaction. As will be appreciated by those skilled in the art, the oxidation of isobutyraldehyde in the liquid bath can be achieved in the absence of a catalyst, although the non-catalytic reaction is disadvantageous in that it frequently leads to dangerous and unacceptable peroxide concentrations in the bath and in the products separated from the bath. For example, non-catalytic operation can result in as much as 150–200 g per liter of peroxides, calculated as perisobutyric acid.

The reaction may be carried out in a wide variety of ways. It is generally preferred that the process be carried out continuously by introducing streams of molecular oxygen-containing gas and of liquid isobutyraldehyde into a heated reaction bath containing the catalyst dissolved in the solvent. The bath is stirred either by mechanical means or by efficiently dispersing the oxygen-containing gas throughout the liquid bath. The turbulence in the bath should be sufficient to ensure intimate contact of the gas with the liquid isobutyraldehyde and solvent.

Recovery of the products of the reaction may conveniently be effected by conventional techniques, such as condensation, washing of the non-condensable gases, ordinary distillation and extractive distillation.

The following examples, which are provided by way of illustration, and not by way of limitation, are illustrative of the principal concepts of the present invention.

EXAMPLE 1

The reactor is a vertical tube made of stainless steel, having a height of 4 meters and an internal diameter of 57 millimeters. This tube is surrounded by a conventional jacket for temperature control by passage therethrough of cooling fluid, such as water, or heating fluid, such as steam. At the bottom of the tube is provided a device for dispersing air throughout the liquid which is a perforated plate provided with seven holes of a diameter of 1.5 mm each.

The reactor is surmounted by a distillation column, of 2.5 meters height filled in with packing materials. The gases and vapors leaving the top of the column are passed through a condenser and an aliquot of the liquid condensed therein is refluxed to the top of the column. This reflux is so controlled as to maintain constant the level of the liquid bath in the reactor. Another purpose of the reflux is to constitute a barrier to prevent the isobutyric acid vapors from escaping from the top of the column.

The starting reaction bath is constituted by 4 liters of isobutyric acid containing in dissolved state 100 ppm by weight of manganese brought into play in the form of its acetate.

The operating conditions are as follows:

| | |
|---|---|
| Temperature of the bath | 123° C |
| Pressures | 1 bar, effective |
| Isobutyraldehyde feed | 880 g/hour |
| Air feed | 2200 Nl/hour |

The total conversion rate of the isobutyraldehyde, per passage, is 79 %.

The molar yields are as follows:

| | |
|---|---|
| Acetone | 62.0 % |
| Isopropanol | 23.0 % |
| Isopropyl formate | 1.5 % |
| Isopropyl isobutyrate | 0.8 % |
| Isobutyric acid | 4.4 % |

The peroxide content of the bath, calculated as perisobutyric acid, is 7 g/liter.

EXAMPLE 2

The operation is carried out in the apparatus of Example 1, with a starting bath constituted by 2.9 liters of isobutyric acid containing in dissolved state 15 ppm by weight of molybdenum brought into play in the form of its isobutyrate.

The operating conditions are as follows:

| | |
|---|---|
| Temperature of the bath | 126° C |
| Pressure, effective | 1 bar |
| Isobutyraldehyde feed | 1440 g/hour |
| Air feed | 2200 Nl/hour |

The total conversion rate of the isobutyraldehyde, per passage, is 72 %.

The molar yields are as follows:

| | |
|---|---|
| Acetone | 57.0 % |
| Isopropanol | 26.0 % |
| Isopropyl formate | 1.2 % |
| Isopropyl isobutyrate | 0.9 % |
| Isobutyric acid | 1.8 % |

The peroxide content of the bath, calculated as periosbutyric acid, is 8 g/liter.

EXAMPLE 3

The operation is carried out in the apparatus of Example 1, with a starting bath constituted by 1 liter of isobutyric acid containing in dissolved state 120 ppm by weight of manganese in the form of manganese isobutyrate and 120 ppm by weight of nickel in the form of nickel isobutyrate.

The operation conditions are as follows:

| | |
|---|---|
| Isobutyraldehyde feed rate | 493 g/hour |
| Air feed rate | 900 liters/hour |
| Temperature of the bath | 125° C |
| Pressure, effective | 3 bar |

The results are as follows:

| | |
|---|---|
| Peroxide content of the bath (reckoned as perisobutyric acid) | 21 g/liter |
| Total conversion rate of the | |

| | |
|---|---|
| isobutyraldehyde, per passage | 64 % |
| Molar yields: | |
| Acetone | 45.2 % |
| Isopropanol | 32.8 % |
| Isopropyl formate | 1.12 % |
| Isopropyl isobutyrate | 2.16 % |
| Isobutyric acid | 5.9 % |

The productivity to acetone is 108 g per hour per liter of bath and the productivity to isopropanol is 81.5 g per hour per liter of bath.

EXAMPLE 4

The operation is carried out in the apparatus of Example 1, with a starting bath constituted by 4 liters of isobutyric acid containing in dissolved state 100 ppm by weight of manganese in the form of its carbonate.
The operation conditions are as follows:

| | |
|---|---|
| Isobutyraldehyde feed rate | 880 g/hour |
| Air feed rate | 2200 liters/hour |
| Temperature of the bath | 125° C |
| Pressure, effective | 1 bar |

The results are as follows:

| | |
|---|---|
| Total conversion rate of the isobutyraldehyde, per passage | 78 % |
| Molar yields: | |
| Acetone | 61.0 % |
| Isopropanol | 24.0 % |
| Isopropyl formate | 1.3 % |
| Isopropyl isobutyrate | 0.7 % |
| Isobutyric acid | 3.8 % |

EXAMPLE 5

The operation is carried out in the apparatus of Example 1, with a starting bath constituted by 4 liters of isobutyric acid containing in dissolved state 1800 ppm by weight of silver in the form of its nitrate.
The operation conditions are as follows:

| | |
|---|---|
| Isobutyraldehyde feed rate | 980 g/hour |
| Air feed rate | 1300 liters/hour |
| Temperature of the bath | 120° C |
| Pressure, effective | 1 bar |

The results are as follows:

| | |
|---|---|
| Total conversion rate of the isobutyraldehyde, per passage | 74 % |
| Molar yields: | |
| Acetone | 39.0 % |
| Isopropanol | 34.5 % |
| Isopropyl formate | 2.0 % |
| Isopropyl isobutyrate | 1.3 % |
| Isobutyric acid | 4.6 % |

EXAMPLE 6

The operation is carried out in the apparatus of Example 1, with a starting bath constituted by 4 liters of isobutyric acid containing in dissolved state 900 ppm by weight of chromium in the form of its naphtenate.
The operation conditions are as follows:

| | |
|---|---|
| Isobutyraldehyde feed rate | 1200 g/hour |
| Air feed rate | 2600 liters/hour |
| Temperature of the bath | 138° C |
| Pressure, effective | 3.5 bar |

The results are as follows:

| | |
|---|---|
| Total conversion rate of the isobutyraldehyde, per passage | 78.5 % |
| Molar yields: | |
| Acetone | 43.5 % |
| Isopropanol | 30.2 % |
| Isopropyl formate | 1.5 % |
| Isopropyl isobutyrate | 1.8 % |
| Isobutyric acid | 5.2 % |

EXAMPLE 7

The operation is carried out in the apparatus of Example 1, with a starting bath constituted by 4 liters of isobutyric acid containing in dissolved state 150 ppm by weight of nickel in the form of its stearate.
The operation conditions are as follows:

| | |
|---|---|
| Isobutyraldehye feed rate | 800 g/hour |
| Air feed rate | 1200 liters/hour |
| Temperature of the bath | 120° C |
| Pressure, effective | 1.5 bar |

The results are as follows:

| | |
|---|---|
| Total conversion rate of the isobutyraldehyde, per passage | 69.5 % |
| Molar yields: | |
| Acetone | 41.0 % |
| Isopropanol | 32.5 % |
| Isopropyl formate | 1.8 % |
| Isopropyl isobutyrate | 1.6 % |
| Isobutyric acid | 6.0 % |

EXAMPLE 8

The operation was carried out as in Example 7, but in the presence of 150 ppm by weight of vanadium in the form of its acetate instead of nickel stearate. The results are the same.

EXAMPLE 9

The operation was carried out as in Example 7, but in the presence of 150 ppm by weight of tungsten in the form of its acetate instead of nickel stearate. The results are the same.

EXAMPLE 10

The operation was carried out as in Example 7, but in the presence of 150 ppm by weight of titanium in the form of its acetate instead of nickel stearate. The results are the same.

EXAMPLE 11

The operation was carried out as in Example 7 but in the presence of 40 ppm by weight of cerium in the form of its acetate instead of nickel stearate. The results are the same.

It will be apparent from the foregoing that we have provided a new and improved process for producing isopropanol and acetone by the reaction of isobutyraldehyde and an oxygen-containing gas in the liquid phase. In the process of the present invention a simple and accurate method is provided for preparing isopropanol and acetone in good yields and with good conversions.

It will be understood that various modifications may be made in the details of formulation and operating conditions without departing from the spirit of the invention, especially as defined in the following claims.

We claim:

1. A process for the production of isopropanol and acetone comprising contacting isobutyraldehyde and a free oxygen-containing gas with a catalyst consisting essentially of a salt selected from the group consisting of the acetate, isobutyrate, carbonate, nitrate, naphthenate and stearate of a metal selected from the group consisting of molybdenum, silver, chromium, manganese, nickel, cobalt, vanadium, tungsten, titanium and cerium, in a liquid medium at a temperature within the range of 100°–170° C.

2. A process as defined in claim 1 wherein the salt is acetate salt.

3. A process as defined in claim 1 wherein the oxygen-containing gas is air.

4. A process as defined in claim 1 wherein the liquid medium contains a solvent for the reactants, the reaction products and the catalyst, the said solvent being chemically inert under the reaction conditions and having a boiling point below 200° C.

5. A process as defined in claim 4 wherein the solvent is isobutyric acid.

6. A process as defined in claim 4 wherein the reaction is carried out at a temperature within the range of 110°–150° C.

7. A process as defined in claim 4 wherein the reaction is carried out at a pressure within the range of 1 to 4 bar, effective.

8. A process as defined in claim 1 wherein the metal catalyst is present in the liquid medium in an amount within the range of 10–2000 ppm by weight.

9. A process as defined in claim 1 wherein the salt is selected from the group consisting of the acetate, isobutyrate, carbonate, nitrate, naphthenate and stearate salts.

* * * * *